United States Patent [19]

Hynson et al.

[11] Patent Number: 5,558,095
[45] Date of Patent: Sep. 24, 1996

[54] METHOD AND DEVICE FOR INCREASING HAND VASCULAR RESISTANCE DURING BLOOD PRESSURE MEASUREMENT

[76] Inventors: James M. Hynson, 1674 32nd Ave., San Francisco, Calif. 94122; Jeffrey A. Katz, 1440 Madera Way, Millbrae, Calif. 94030

[21] Appl. No.: 520,140

[22] Filed: Aug. 25, 1995

Related U.S. Application Data

[63] Continuation of Ser. No. 297,301, Aug. 29, 1994.

[51] Int. Cl.⁶ .................................................. A61B 5/00
[52] U.S. Cl. ........................ 128/668; 128/672; 128/748
[58] Field of Search .................................. 128/607, 668, 128/672, 748

[56] References Cited

PUBLICATIONS

Pauca, "Effect of Pethidine Premedication and Halothene Anesthesia on Upper Limb blood flow," *British Journal of Anesthesia*, vol. 68, 1992, pp. 621–622.

Pauca, "Upper Limb Blood Flow During Hetamethonium Induced Hypotension" British Journal of Anesthesia, vol. 60, 1988, pp. 151–156.

Hynson et al, "Thermoregulatory and Anesthetic–Induced Alterations in the Differences Among Femoral, Radial, and Oscillometric Blood Pressures" *Anesthesiology*, vol. 81, No. 6, Dec. 1984, pp. 1411–1421.

Pauca et al, "Reliability of the Radial Arterial Pressure During Anesthesia: Is Wrist Compression a Possible Diagnostic Test?" Chest, Jan. 1994, vol. 105/1, pp. 69–75.

*Primary Examiner*—Angela D. Sykes
*Assistant Examiner*—Robert L. Nasser, Jr.
*Attorney, Agent, or Firm*—William W. Jones

[57] ABSTRACT

The vascular resistance to blood flow through the hand is increased in an essentially uniform manner by the application of pressure to the hand. The pressure is applied by means of an inflatable bladder mounted on an arm board or within a non-expandable sleeve, mitten or glove, which bladder covers at least the palm of the hand. Controlled inflation of the bladder conveys pressure to the hand tissue to a degree necessary to compress vascular structures and obstruct or restrict blood flow. By occluding blood flow through the hand, more accurate invasive blood pressure readings can be taken in clinical situations where decreased hand vascular resistance occurs.

3 Claims, 1 Drawing Sheet

METHOD AND DEVICE FOR INCREASING HAND VASCULAR RESISTANCE DURING BLOOD PRESSURE MEASUREMENT

This is a division of copending U.S. Ser. No. 08/297,301, filed Aug. 29, 1994.

TECHNICAL FIELD

This invention relates to a method and apparatus for occluding blood flow through the arterio-venous shunts in the hand so as to enable accurate invasive blood pressure measurements to be obtained from the patient's forearm. More particularly, this invention relates to a method and apparatus for uniformly occluding blood flow through the hand by applying external pressure to the hand by means of a selectively inflatable bladder which covers at least the palm of the hand.

BACKGROUND ART

The physiologic basis for a wide variation in hand blood flow is the effect of the thermoregulatory shunts on hand vascular resistance. The thermoregulatory shunts are present in the fingers and palms. During thermoregulatory vasoconstriction, these shunts are tightly closed and hand blood flow is primarily determined by nutritional needs. During thermoregulatory vasodilation, the shunts are open and provide a low resistance arterio-venous path. During such vasodilation periods, blood pressure measured invasively at the radial artery may not accurately reflect central aortic pressure because the large increase in blood flow along the brachial and radial arteries leads to a significant pressure gradient from proximal to distal locations in the circulatory system.

There are a number of clinical situations when a patient's blood pressure will be monitored invasively by means of an arterial blood pressure line inserted in the patient's forearm, specifically, in the radial artery. These situations include during surgery; in intensive or critical care units; in cardiac care units; and in surgical recovery units, for example. There are a number of common clinical situations in which problems arise in obtaining accurate arterial blood pressure measurement from the invasive arterial blood pressure line in the patient's forearm due to increased blood flow through the hand, particularly through arterio-venous shunts. These include anesthesia-induced vasodilation, hemodilution, use of potent vasodialtors, sepsis, and hyperthermia. Several of these conditions are present at the termination of cardiopulmonary bypass surgery. The inability to accurately monitor arterial blood pressure at a distal location by invasive means due to the presence of a significant pressure gradient in the aforesaid clinical situations is a problem which has not been addressed in a practical manner to date.

It would be highly desirable to provide a practical and readily controlled method and apparatus for lessening the proximal-to-distal pressure gradient in a patient's circulatory system to a degree wherein distal invasive pressure measurements could be obtained which accurately reflect aortic pressure.

DISCLOSURE OF THE INVENTION

This invention relates to a method and apparatus for selectively and uniformly occluding blood flow through distal arterio-venous shunts located in one's hand to a degree that will enable accurate arterial blood pressure measurements to be made invasively from the radial artery in the forearm during periods of hand vasodilation. The method preferably involves the application of a uniform external pressure to at least the palm of the hand so as to squeeze the hand sufficiently to occlude blood flow to a degree which essentially prevents blood from flowing through the arterio-venous shunts in the hand. By preventing or severely restricting blood flow through the shunts, the resistance to blood flow through the remainder of the arm is increased so that the blood pressure in the arm, and particularly in the radial artery will more closely match the aortic blood pressure.

The aforesaid external pressure is preferably applied to the hand by means of an inflatable bladder which is positioned over at least the palm of the hand. The bladder will have one component which faces away from the hand and which is relatively non-stretchable so that it will not expand away from the band when the bladder is inflated. The bladder will have another component which contacts the palm of the hand and which is elastic so that it will expand against the palm of the hand when the bladder is inflated. The back of the hand will be restrained either by a non-elastic component or sleeve on the bladder, or by an arm board which is fastened to the patient's arm and hand. The bladder can be inflated manually by means of a manually operated inflation bulb, or automatically by means of an automated pump. The automated pump can be included in an otherwise conventional automated non-invasive blood pressure monitor which may be concurrently used to derive blood pressure readings from the patient's upper arm. At times when the blood pressure readings are desired from an invasive line inserted into the patient's radial artery, the hand-pressurizing bladder will be inflated to pressures which preferably exceed the patient's systolic blood pressure. When the hand has been sufficiently occluded, the radial artery blood pressure measurements will be taken. When the measurement procedure is finished, the bladder can be deflated until the next time one desires to obtain the radial artery blood pressure readings.

It is therefore an object of this invention to provide a method and apparatus for use in uniformly increasing vascular resistance to blood flow in the hand in order to obtain more reliable invasive distal blood pressure measurements in the arm.

It is a further object of this invention to provide a method and apparatus of the character described which involves applying a relative uniform pressure to the exterior of the hand during periods of time when blood pressure measurements are taken.

It is another object of this invention to provide a method and apparatus of the character described wherein an inflatable bladder is selectively and uniformly inflated on the hand so as to compress the palm of the hand sufficiently to obtain the desired degree of vascular resistance to blood flow in the hand.

It is yet another object of this invention to provide a method and apparatus of the character described wherein the bladder is mounted on an arm board or forms a part of a structure which encircles the hand and can be used to constrain the hand relative To the bladder so as to ensure the application of uniform pressure to the hand by the bladder.

These and other objects and advantages of the invention will become more readily apparent from the following detailed description of several embodiments of the invention when taken in conjunction with the accompanying drawings in which:

DETAILED DESCRIPTION OF SPECIFIC EMBODIMENTS OF THE INVENTION

Figure 1:
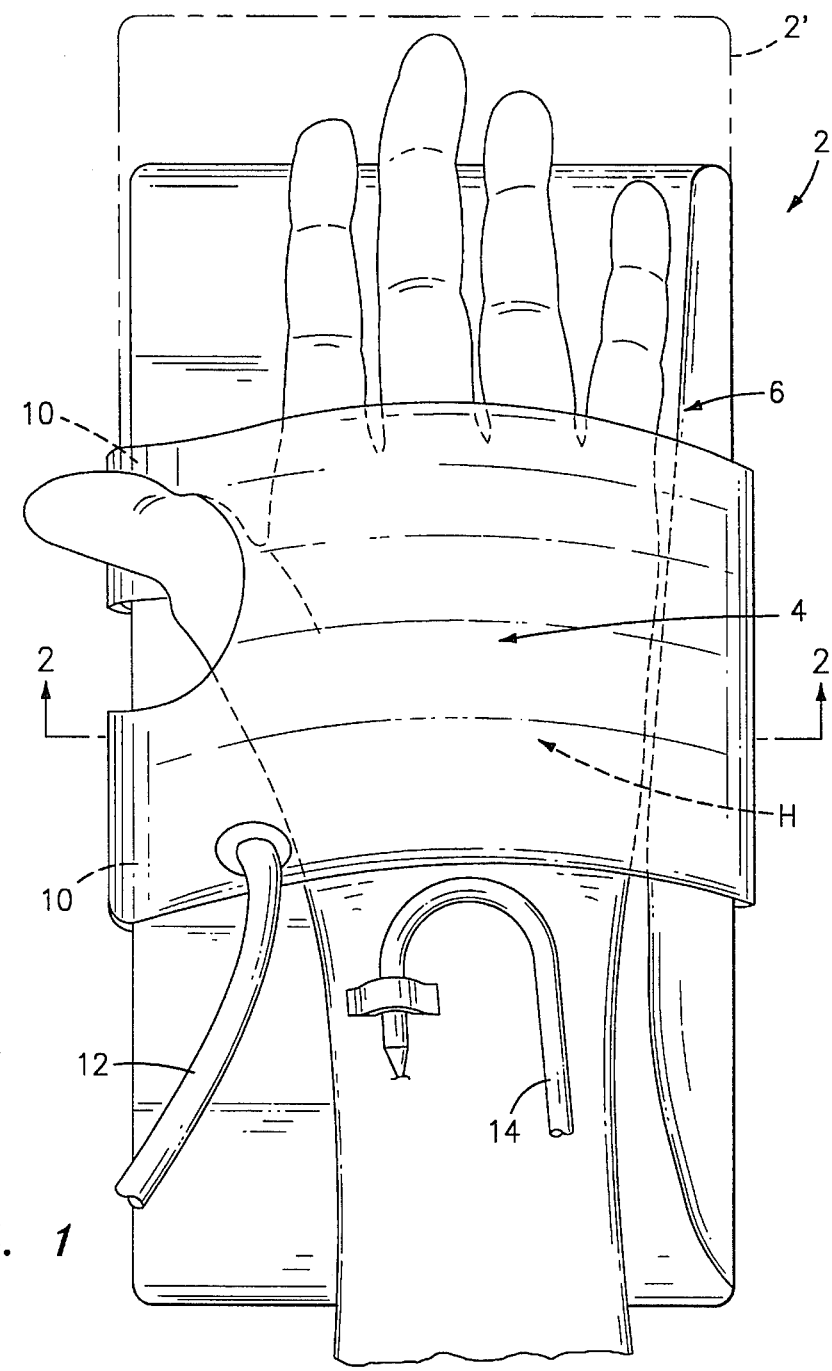
FIG. 1 is a plan view of an embodiment of the device used to retard or occlude blood flow in the hand.

Referring now to the drawings there is shown in FIG. 1 an example of a blood flow retarding or restricting device formed in accordance with this invention. The device is denoted generally by the numeral 2 and includes an inflatable portion 4 which overlies at least the palm of the hand H, and a hand constricting portion 6 which covers the back of the hand H. In the embodiment shown in FIG. 1, the constricting portion 6 is an arm board to which the arm of the patient is strapped; however, the constricting portion 6 could also take the form of a non-elastic web or the like which covers the back of the hand H. One side of the inflatable portion 4 may be fixed to the arm board 6 as at 8, and the other side of the inflatable portion 4 may be releasibly secured to the arm board 6 by closures such as hook and loop assemblies 10. This arrangement will easily allow the device 2 to be affixed to or removed from the hand H. This embodiment of the device 2 is designed to cover only the palm of the hand H; However, the palm, thumb and fingers could be covered by the device as indicated by the phantom line 2'. When a finger-covering embodiment is utilized, the inflatable portion 4 can be permanently connected to the constricting portion 6 throughout the entire overlying margin of the two portions so as to form, in effect, a mitten-like device having an inflatable side and an opposite constricting side. The inflatable portion 4 is provided with an inflation/deflation hose 12 which is connected to a manually or automated inflating device (not shown) so that the portion 4 can be selectively inflated and deflated as desired. The line used for invasively measuring the patient's arterial blood pressure is indicated by the numeral 14 and communicates with the patient's radial artery in the vicinity of the patient's wrist.

Figure 2:
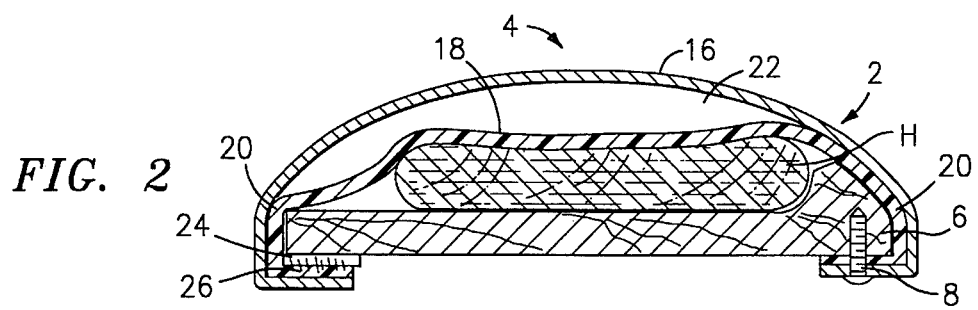
FIG. 2 is a sectional view through the device showing the edge seals for the bladder and the manner of construction of the remaining components of the device.

Referring now to FIG. 2, details of the construction and assembly of the various components of the device 2 are shown in detail. As seen in FIG. 2, the hand H is embraced by the arm board 6 and the inflatable portion 4 which overlies the hand H. The inflatable portion 4 includes an outer non-elastic part 16 and an inner elastic part 18, the latter of which contacts the hand H. The parts 16 and 18 are joined at their margins 20 so as to form a bladder having an internal inflatable chamber 22. Strips 24 and 26 of the hook and loop closure 10 are adhered to the inflatable portion 4 and the arm board 6 respectively so that, when the strips 24 and 26 are pressed together, the inflatable portion 4 will be held in the position shown in FIG. 2 overlying the hand H. When the chamber 22 is pressurized, the elastic part 18 of the device will press the hand H tightly against the arm board 6 so as to restrict or occlude blood flow through the hand H.

The device 2 can be operated in the following manner. The patient's arm and hand H will be secured to the arm board in a normal manner, and the blood pressure line 14 will be properly implanted in place in the patient's forearm. The portion 4 of the device 2 will be brought into overlying position relative to the patient's hand, and the closure strips 24 and 26 will be pressed together. At such times as it is desired to obtain the patient's blood pressure measurements via the line 14, the portion 4 will be pressurized so as to inflate the chamber 22 and press the elastic part 18 of the device 2 against the hand H. The chamber 22 will preferably be pressurized to a pressure which is greater than the estimated systolic pressure of the patient, thereby essentially occluding blood flow through the patient's hand. This will provide increased resistance to blood flow in the arm so as to elevate the blood pressure in the distal portions of the arm to a value which will be comparable to actual aortic blood pressure. While the hand is thus compressed, the invasive blood pressure readings will be obtained through the line 14. At such times when distal invasive blood pressure is not being monitored by the line 14, the device can be deflated to allow blood flow through the hand.

It will be readily appreciated that this invention will allow the taking of more accurate distal invasive blood pressure readings which will be more indicative of actual aortic blood pressure during periods when uncontrollable vasodilation of the blood vessels and shunts in the hand are experienced. The actual cardiovascular condition of the the patient is thus more accurately observed from the distal blood pressure readings so that aortic cardiovascular abnormalities will be more apparent and more readily detected by the invasive distal blood pressure readings. The device can be used in conjunction with non-invasive blood pressure monitors as a periodic confirmation or check of the accuracy of the non-invasive blood pressure readings_ As previously noted, the device may be configured without an arm board and may rely on a constricting sleeve which covers the back of the hand. The device could also take the form of a glove or mitten with or without the arm board, which covers the entire hand of the patient.

Since many changes and variations of the disclosed embodiments of the invention may be made without departing from the inventive concept, it is not intended to limit the invention otherwise than as required by the appended claims.

What is claimed is:

1. A method for obtaining accurate blood pressure readings from a patient's radial artery during periods of vasodilation of blood vessels in the hand, said method comprising the steps of:

a) applying uniform pressure to the patient's hand so as to uniformly restrict blood flow in the patient's hand to a degree necessary to elevate blood pressure in a distal portion of the patient's arm to a level which is comparable to aortic blood pressure; and b) invasively measuring the patient's blood pressure in the radial artery in said distal portion of the patient's arm while continuing to restrict blood flow in the patient's hand.

2. The method of claim 1 wherein the uniform pressure is applied by confining at least the palm of the patient's hand in an inflatable device, and inflating the device to compress the palm of the hand so as to restrict blood flow in the patient's hand.

3. The method of claim 2 wherein the device is inflated to a pressure which equals or exceeds the expected systolic blood pressure of the patient.

* * * * *